(12) United States Patent
Herry et al.

(10) Patent No.: US 10,111,869 B2
(45) Date of Patent: Oct. 30, 2018

(54) REDUCTION OF OPIOID BLOOD FLUCTUATIONS

(71) Applicant: ETHYPHARM, Saint-Cloud (FR)

(72) Inventors: Catherine Herry, Saint-Ouen du Tilleul (FR); Maryline Boyer, Louveciennes (FR); Francoise Vauzelle-Kervroedan, Les Molieres (FR); Pascal Oury, Le Chesnay (FR)

(73) Assignee: ETHYPHARM, Saint-Cloud (FR)

( * ) Notice: Subject to any disclaimer, the term of this patent is extended or adjusted under 35 U.S.C. 154(b) by 79 days.

(21) Appl. No.: 14/250,785

(22) Filed: Apr. 11, 2014

(65) Prior Publication Data

US 2014/0220127 A1   Aug. 7, 2014

Related U.S. Application Data

(63) Continuation of application No. 13/377,750, filed as application No. PCT/EP2010/058323 on Jun. 12, 2010, now abandoned.

(60) Provisional application No. 61/213,483, filed on Jun. 12, 2009.

(30) Foreign Application Priority Data

Jun. 12, 2009  (FR) ..................... 09 53951

(51) Int. Cl.
*A61K 31/485*  (2006.01)
*A61K 9/20*  (2006.01)
*A61K 9/28*  (2006.01)

(52) U.S. Cl.
CPC .......... *A61K 31/485* (2013.01); *A61K 9/2027* (2013.01); *A61K 9/2054* (2013.01); *A61K 9/2077* (2013.01); *A61K 9/2866* (2013.01)

(58) Field of Classification Search
CPC .. A61K 31/485; A61K 9/2027; A61K 9/2054; A61K 9/2077; A61K 9/2866
See application file for complete search history.

(56) References Cited

U.S. PATENT DOCUMENTS

| | | |
|---|---|---|
| 4,861,598 A | 8/1989 | Oshlack |
| 4,970,075 A | 11/1990 | Oshlack |
| 2009/0011016 A1* | 1/2009 | Cailly-Dufestel et al. ... 424/465 |

FOREIGN PATENT DOCUMENTS

| | | |
|---|---|---|
| EP | 0 609 961 A1 | 8/1994 |
| WO | WO 96/00066 | 1/1996 |
| WO | WO 2004/084868 A1 | 10/2004 |
| WO | WO 2007/099152 A1 | 9/2007 |
| WO | WO 2007/099154 A1 | 9/2007 |

OTHER PUBLICATIONS

International Search Report in Application No. PCT/EP2010/058323, dated Nov. 17, 2010.

* cited by examiner

*Primary Examiner* — Hasan S Ahmed
(74) *Attorney, Agent, or Firm* — Dinsmore & Shohl LLP

(57) ABSTRACT

The present invention relates to the use of a sustained release matrix containing at least one opioid for producing a solid oral formulation in table form suitable for reducing blood concentration fluctuations of said opioid.

10 Claims, 3 Drawing Sheets

REDUCTION OF OPIOID BLOOD FLUCTUATIONS

This application is a Continuation application of U.S. patent application Ser. No. 13/377,750, filed Dec. 12, 2011, which is a 371 application of International Application No. PCT/EP2010/058323, filed Jun. 12, 2010, and claims benefit to U.S. Provisional Application 61/213,483, filed Jun. 12, 2009, and also claims priority to French Patent Application 0953951, filed Jun. 12, 2009, all of which are incorporated by reference in its entirety herein.

The subject of the present invention is a matrix-type tablet for the sustained release of at least one opioid for its use as medicinal product to lower fluctuations in the plasma concentrations of said opioid.

It is well known that when opioids are administered orally, they are efficient only if they are given at a sufficient frequency and at sufficiently high doses.

The activity of opioids in humans is directly related to the plasma concentration of the opioids. Also, there is a general relationship between the increase in plasma concentration of opioids and the increasing occurrence of adverse side effects related to the dosage, in particular nausea, vomiting, drowsiness and respiratory depression.

Thus, for the treatment and control of pain through the use of dosage forms containing active ingredients such as opioids, it is necessary that said active ingredient is released over extended periods of time in order to provide an efficient therapeutic effect. It is also desired that pharmaceutical formulations comprising opioids provide a sufficient dose while avoiding large changes in plasma concentrations (peak to trough) and episodes of resurgent pain or breakthrough pain in patients.

Of potent opioids, morphine is thought to be the most preferred molecule for treating severe pain. Morphine is suitably absorbed orally, but is subjected to a strong hepatic extraction, so that its bioavailability can decrease down to 20-30%.

Several pharmaceutical forms of morphine are commercially available for example under the names Skenan® and Moscontin®. These pharmaceutical formulations have a duration of action of 12 hours, and contain 10, 30, 60, 100 mg or 200 mg of morphine sulfate. These pharmaceutical forms should be administered at least twice a day.

Kapanol®, in granule dosage form filled in capsules to 20, 50 or 100 mg, has a duration of action of 24 hours.

There are other strong opioids such as hydromorphone or oxycodone.

Hydromorphone (Sophidone® at 4, 8, 16 and 24 mg) is a semi-synthetic morphine derivative having an analgesic potency about 7.5 times higher than morphine. It is an oral alternative to morphine. It is indicated for cancer-related severe pain, in the event of resistance and/or intolerance (examples: cognitive deficiency, drowsiness and hallucinations) or resistance to morphine.

Oxycodone is a semi-synthetic morphine derivative having an analgesic potency about twice that of morphine. It is an oral alternative to morphine for various pharmacological reasons, especially in case of resistance or intolerance.

It is commercially available in a sustained-release (Oxycontin LP® or Oxygesic® 10, 20 and 40, 80 mg) and immediate-release (Oxynorm® 5, 10, 20 mg) form. The marketing authorization (AMM) states that it is reserved for treating cancer-related severe pain or in case of resistance or intolerance to morphine.

WO2004084868 can also be cited which discloses a sustained-release pharmaceutical form comprising a matrix based on a polyethylene glycol, a polyethylene oxide and an ethylene oxide block copolymer including an opioid and a coating based on cellulose derivatives which releases over 75% of the opioid between 4 and 10 hours with zero order kinetics. This document further teaches that the commercially available compositions MS Contin® (administered twice a day) and Kadiane (administered once a day) show fluctuations of plasma concentrations such that the minimum plasma concentration is lower than half the peak plasma concentration.

EP0609961 discloses a sustained-release pharmaceutical composition comprising a core containing an opiate agonist and a coating containing a polymer insoluble at all pH values, a compound soluble in an acid at a pH value of 1 to 4 and an enteric-soluble polymer, essentially insoluble at a pH value of 1 to 4, said composition releasing the opiate, at a steady state, with a $T_{max}$ of 4.5 hours or more.

WO 96/00066 discloses controlled-release morphine tablets for oral administration. These tablets are obtained by sequential compression of two compositions: a first so-called "therapeutic" composition obtained by wet granulation of a mixture containing morphine sulfate, one or more polyalkylene oxides and polyvinyl pyrrolidone, and a second composition obtained by wet granulation of a mixture containing a polyalkylene oxide, sodium chloride and hydroxypropyl methyl cellulose. The resulting tablet comprises a composition of active ingredient coated with a porous semi-permeable membrane for controlling the release rate of said active ingredient.

U.S. Pat. Nos. 4,861,598 and 4,970,075 disclose sustained-release pharmaceutical compositions which can include oxycodone. The pharmaceutical compositions disclosed contain as excipients an aliphatic alcohol having 10-18 carbon atoms and an acrylic resin. In one exemplified composition, 43% of oxycodone is released within one hour and 100% within 5 hours; in another example, 16% of oxycodone is released within one hour and 100% within 9 hours.

Application WO2007/099154 filed by the Applicant, describes water-insoluble matrix-type tablets capable of releasing oxycodone into the body over an extended time period, preferably over periods of more than 12 hours and further preferably more than 20 hours.

The matrix-type tablets coated with ethylcellulose, also called "«QD» tablets which are described in application WO2007/099154 were developed to be administered in once-a-day form.

One essential object of the present invention is therefore to improve the control of pain by using sustained-release opioid pharmaceutical formulations having pharmacokinetic performance such that the fluctuations of plasma concentrations of opioids are greatly reduced.

DEFINITIONS

The term "matrix-type tablet" is used in the invention to designate a tablet whose inner structure is homogeneous and identical from the centre towards the periphery of the tablet. Therefore, the tablets of the present invention consist of a homogeneous mixture of active ingredient in powder or granule form and of a compression matrix containing at least one excipient chosen from the group comprising sustained-release, pH-independent and water-insoluble polymers, mineral excipients and their mixtures.

The term "compression matrix" in the present invention is used to designate all the excipients which take part in the cohesion of the tablet. Said compression matrix is both water-insoluble and has a certain permeability (hydrophilic matrix) or porous network (inert matrix) responsible for the sustained release of the active ingredient, which does not vary in relation to the pH conditions of the medium.

The term "compression mixture" is used in the present application to designate all the constituents of the tablets (the active ingredient(s), granulated or not, and the constituents of the compression matrix) before its compression in tablet form.

As used in the present invention, the term "steady-state" refers to the steady pharmacokinetic state which is achieved after repeated doses of the same dosage form. This steady state is generally achieved after 4 to 5 drug half-lives, with plasma concentrations of the opioid varying between $Css_{max}$ and $Css_{min}$.

A study with repeat doses not only provides a measure of the usual bioavailability parameters (AUCss, $Css_{max}$, $Tss_{max}$), but also demonstrates the significance of the fluctuations between the steady-state peak ($Css_{max}$) and trough ($Css_{min}$) concentrations.

The $C_{max}$ or peak plasma concentration is the peak concentration representing the highest point of the plasma concentration in the whole kinetics. This peak is measured after administration of a single dose of opioid.

$C_{SSmax}$ designates the steady-state peak plasma concentration.

$T_{max}$ is the time to reach the peak concentration. This value is indicative of the absorption rate of a pharmaceutically active material.

$T_{SSmax}$ designates the time to reach the steady-state peak plasma concentration.

The pharmacokinetic parameters $C_{max}$ and $T_{max}$ result directly from experimental plots.

Repeat dosing with a drug can involve a certain accumulation of the drug, or its metabolites, the significance of which depends on the dosage schedule used.

Given a drug M, administered orally at a dose D at a dosing time interval τ. As the drug is given before the previous dose is fully eliminated, the amount administered adds to the non-eliminated amount from the previous doses (superimposition principle). After a period of time, the amount of drug absorbed enters into a certain equilibrium absorption rate with the amount of drug eliminated during the period τ; a steady state is thus achieved. Any further dosing of the product during the period τ will no longer change this state. Concentrations vary between a trough concentration $Css_{min}$ and a peak concentration $Css_{max}$. When the intake rate is in perfect equilibrium with the elimination rate, this steady state is represented by a pseudo-plateau, where the $Css_{max}$ and $Css_{min}$ values are thus very similar.

As used in the present invention, "repeat oral dosing" refers to administration of the formulation of the present invention at a dose D at a dosing time interval τ of between 8 and 14 hours, preferably between 11 and 13 hours and further preferably of 12 hours.

The "fluctuation" and "swing" parameters are expressed as a % and are calculated according to the following equations:

$$100*(C_{max}-C_{min})/Cav \qquad \text{Fluctuation:}$$

wherein Cav is the "concentration average", representing the AUC over the time interval divided by the time interval: $Cav=AUC_{\tau/\tau}$ In the meaning of the present invention, the expression «reduction of fluctuations» may designate the lowering of the number of peaks and troughs, or preferably a value for the «fluctuation» parameter of between 25% and 50% or more preferably less than 25%.

$$100*(C_{max}-C_{min})/C_{min}=\Delta \qquad \text{Swing:}$$

By a plasma profile showing «peaks and troughs» is meant a plasma profile with highly pronounced modulations, the peak possibly corresponding to Cmax and the trough to a plasma concentration obtained after elimination of the active ingredient.

It is therefore most advantageous to provide a form with modified release allowing a plateau plasma concentration profile to be obtained, which could be achieved after perfusion at constant flow rate, to level out the phenomena of peaks and troughs.

The half-life time T½ is the time for a concentration C of a drug in a body fluid or a tissue to reach the concentration C/2.

The area under the curve, AUC, corresponds to the integral of the plasma concentration over a given time interval.

The AUC is expressed in units of mass (mg, g)×liter$^{-1}$× hour, and is a measure of the bioavailability of a drug.

In the meaning of the present invention, by a profile having «reduced fluctuation» is meant a profile having a swing Δ of less than 50% and which can be likened to the plateau of concentrations which would be obtained after intravenous administration (IV) of an opioid.

In the meaning of the present invention, by a profile having «reduced fluctuation» is also meant a plasma profile maintained above 60% or preferably above 75% of the $C_{SSmax}$ value for at least 10 hours.

As used in the present invention, "calculated pharmacokinetic profile" refers to the "interpolation-addition" model, where the profile resulting from addition and superimposition every τ hours of the kinetic profile obtained in humans after a single dose of the product. The calculation method may be either manual or automated with the use of a Pharmacokinetic Win Non Lin® software, more particularly the "non-parametric superimposition" tool of this software.

Figure 1:
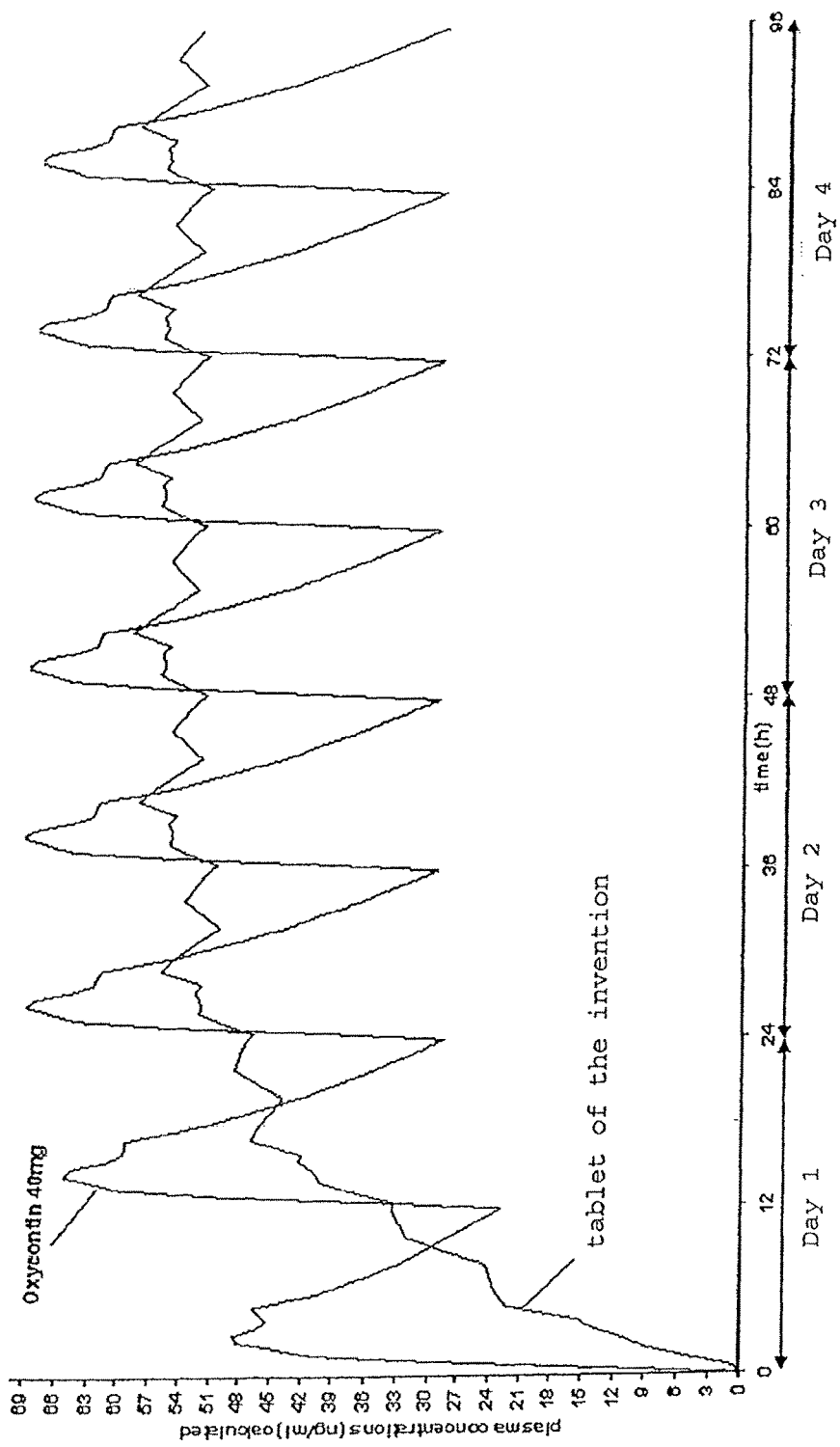
FIG. 1 illustrates steady-state plasma profiles of oxycodone, calculated by the "Interpolation-Addition" method, of 40 mg oxycodone tablets according to the invention and 40 mg oxycodone tablets of the reference drug Oxycontin®.
Figure 2:
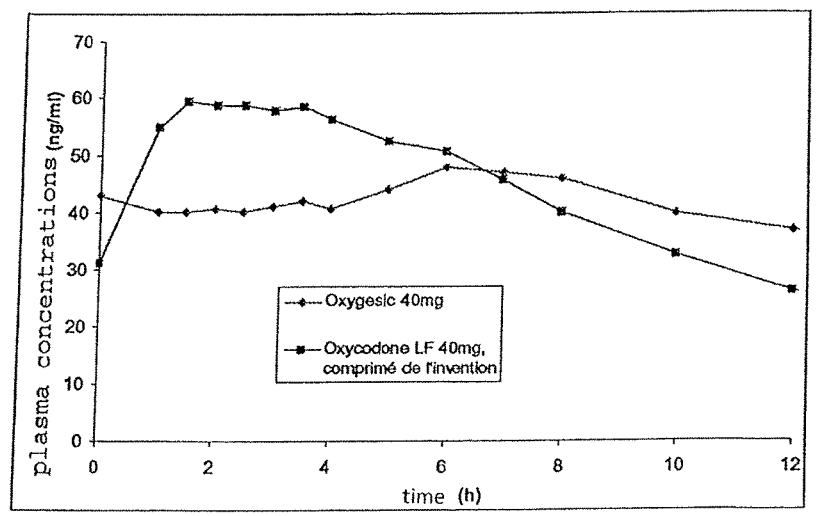

FIG. 2 illustrates, in a steady state (after 5.5 administration days i.e. 11 doses) the mean plasma profiles observed after repeat administrations of 40 mg Oxycodone twice-a-day to healthy volunteers: 40 mg oxycodone tablets according to the invention and 40 mg oxycodone tablets of the reference drug Oxycontin®, over the dosing period (12 hrs) (i.e. the first 12 hours of day 6).

Figure 3:
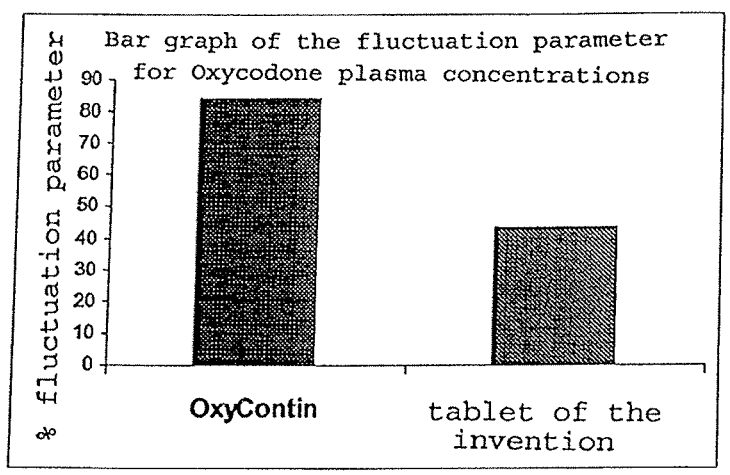
Figure 3:
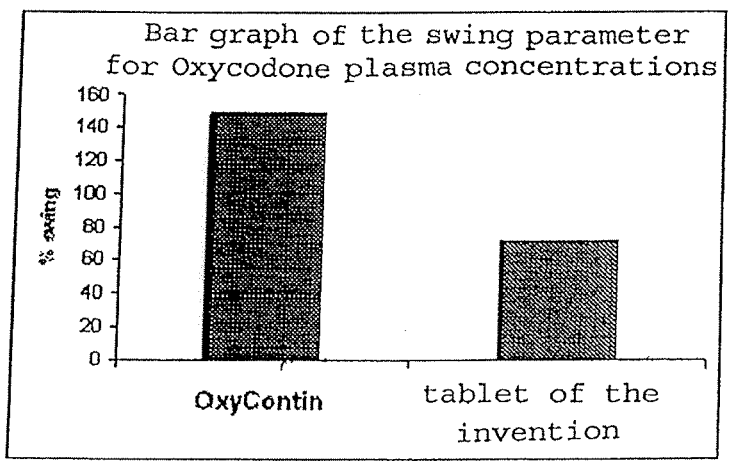

FIG. 3 illustrates the observed "fluctuation and swing" parameters (mean of individual parameters) after administration to healthy volunteers for 5.5 days (11 doses) at intervals of 12 hours of 40 mg oxycodone tablets according to the invention and 40 mg oxycodone tablets of the reference drug Oxycontin®.

DETAILED DESCRIPTION OF THE INVENTION

It has been found within the scope of this invention that formulations prepared in the form of a sustained-release matrix-type tablet can be used for repeat twice-a-day administration to humans, such that the steady-state opioid plasma concentration obtained in vivo is maintained, with reduced fluctuation, at more than 60%, preferably more than 75%, of the $Css_{max}$ value for at least 10 hours, preferably at least 12 hours i.e. throughout the entire time period τ and more preferably from 12 hours to 20 hours.

Therefore, the invention concerns a matrix-type tablet with sustained release of at least one opioid or of one of its pharmaceutically acceptable salts, the compression matrix of said matrix-type tablet consisting of at least one excipient chosen from the group comprising sustained-release, pH-independent, water-insoluble polymers, mineral excipients and their mixtures, for its use as medicinal product administered orally and in repeat two-a-day form spaced apart by 8 to 14 hours, preferably 11 to 13 hours and further preferably by 12 hours.

The invention also concerns the use of a matrix-type tablet for the sustained release of at least one opioid or of one of its pharmaceutically acceptable salts, the compression matrix of said matrix-type tablet consisting of at least one excipient chosen from the group comprising sustained-release, pH-independent, water-insoluble polymers, mineral excipients and their mixtures for the manufacture of a medicinal product administered orally and in repeat to-a-day form spaced apart by 8 to 14 hours, preferably 11 to 13 hours and further preferably by 12 hours.

Advantageously, said medicinal product is intended to treat pain.

Advantageously, the tablet according to the invention allows a steady-state opioid plasma concentration to be maintained in vivo with a reduced fluctuation above 60% of the $C_{SSmax}$ value, preferably above 75% of the $Css_{max}$ value for more than 8 hours, preferably for at least 10 hours, and further for preferably for at least 12 hours. Such a result has not been reported up to now with the prior art granule-type or tablet-type, immediate-release or slow-release formulations, at one or two daily doses.

The use of matrix-type tablets according to the invention allows pharmacokinetics, in the steady-state, to be reached similar to that of perfusion at constant flow rate (where the intake rate balances the elimination rate), with minimum variations in the opioid plasma concentrations. Reducing plasma fluctuations should therefore decrease the peaks and troughs, and accordingly limit the episodes of acute pain (breakthrough pain).

The sustained-release matrix of the matrix-type tablet used according to the invention consists of at least one excipient chosen from the group comprising sustained-release, pH-independent and/or water-insoluble polymers, mineral excipients and their mixtures.

Advantageously the use of the sustained-release, matrix-type tablets of the present invention allows a steady-state to be reached after administration every 10 to 14 hours, preferably every 12 hours.

Advantageously, the use of the sustained-release matrix-type tablets according to the invention firstly gives a "swing" parameter of less than 50%, preferably less than 25%, and secondly a "fluctuation" parameter of less than 50%, preferably less than 25%, in a steady state after repeated dosing every 10 to 14 hours or every 12 hrs.

More advantageously, with using at intervals of 10 to 14 hours, preferably of 12 hours, of the sustained-release matrix-type tablets of the present invention it is possible to observe variations in steady-state concentrations (the difference between $Css_{max}$ and $Css_{min}$) reduced to below 30% of the $C_{max}$ value, preferably reduced to below 20% of the $C_{max}$ value and further preferably reduced to about 14%.

Even more advantageously, the use of the sustained-release matrix-type tablets of the invention provides a decrease in plasma fluctuations, a decrease in the peaks and troughs, and therefore limits resurgent pain related to concentration drops, or even limits the episodes of acute pain (breakthrough pain). Due to reduced values of peak concentrations, the use of the present invention decreases some side effects such as nausea, drowsiness or other cognitive side effects.

The use of the sustained-release matrix-type tablets of the invention provides opioid dissolution and release of less than 30% within 4 hours, less than 80% within 16 hours, as measured according to the rotary paddle method at 100 rpm according to US Pharmacopoeia, in a dissolution medium consisting of 900 mL of an aqueous medium, pH 6.8, so that the in vivo opioid $C_{max}$ value is obtained within 8 to 14 hours and preferably 10 to 12 hours after a single dose of the formulation.

The tablets according to the invention provide time-sustained release of the opioid active ingredient(s) contained in said matrix. The tablets according to the invention thus provide release of the active ingredient in the body for a period of time of more than 8 hours, preferably more than 12 hours, further preferably more than 20 hours.

Advantageously, the compression matrix of the tablets according to the invention represents 50 to 98% by weight of the total weight of the tablets, more advantageously 85 and 95% by weight of the total weight of said tablets.

The sustained-release, water-insoluble and pH-independent polymers which can be used alone or in a mixture in the matrix of the tablets according to the invention can be of an organic nature; in this case they belong to the group comprising cellulose derivatives and especially microcrystalline cellulose (for example such as the one supplied under the trade mark Avicel®, and ethylcellulose (for example the one supplied under the trade mark Aqualon® ethylcellulose), polymers from the class of water-insoluble and non-pH dependent methacrylic acids and in particular the grades Eudragit®RL 12.5, RL PO and RL 100 and RS 12.5, RS PO and RS 100, polyvinylalcohol derivatives, polymers of lactic and glycolic acids (PLGA), starches such as natural starches e.g. corn starches and modified starches such as pre-gelled starch, waxes such as white or yellow beeswax, polyvinyl acetate derivatives, polyvinyl pyrrolidone derivatives, and polymer mixtures such as a mixture of microcrystalline cellulose and polyvinyl acetate/polyvinyl pyrrolidone (80:20) (supplied under the trade mark Kollidon®SR) and a mixture of microcrystalline cellulose and [poly(ethyl acrylate/methyl methacrylate/trimethylamonioethyl methacrylate chloride) (1:2:0.2)].

Advantageously, the sustained-release, water-insoluble and pH-dependent polymers of the present invention belong to the group comprising cellulose derivatives, a mixture of microcrystalline cellulose and [polyvinyl acetate/polyvinyl pyrrolidone (80:20) (supplied under the trade mark Kollidon®SR and a mixture of microcrystalline cellulose and of [poly(ethyl acrylate/methyl methacrylate/trimethylamonioethyl methacrylate chloride) (1:2:0.2)].

The excipients of the compression matrix can also be of mineral type; in this case they belong to the group comprising calcium phosphates (in particular dicalcium or tricalcium phosphates), aluminum and silicon silicates, and magnesium carbonates.

The compression matrix of the tablets according to the invention can advantageously consist of a mixture of several of the above-mentioned excipients. They may include a mixture of organic polymers such as microcrystalline cellulose and vinyl derivatives in varying proportions, or a mixture of an organic polymer with a mineral derivative such as for example a mixture of calcium silicate and silicon with microcrystalline cellulose in varying proportions. The excipients in the compression matrix of the tablets according to the present invention advantageously represent between 40 and 100% by weight of the total weight of said matrix, advantageously from 50 to 90% by weight of the total weight of the matrix.

According to one preferred embodiment of the invention, the compression matrix is a mixture (1:1) of two polymers, advantageously it consists of a mixture (1:1) of microcrystalline cellulose and a 80:20 mixture of polyvinyl acetate/polyvinyl pyrrolidone (supplied under the trade mark Kollidon® SR, or a mixture of microcrystalline cellulose and [polyethyl acrylate/methyl methacrylate/trimethylamonioethyl methacrylate chloride (1:2:0.2)]. Advantageously these two polymers each represent a weight percentage of between 35 and 45% of the total weight of said compression matrix.

The compression matrix can advantageously include, additionally to the excipients of the compression matrix, one or more excipients intended either to promote the proper conducting of the compression process e.g. anti-adherent agents such as colloidal silica, talc, magnesium stearate, Polyethylene Glycol (PEG) or calcium stearate, or to improve the cohesion of the tablets during compression, such as the binders traditionally used for this purpose, in particular starches, cellulose derivatives, or fillers, or lubricants, or plasticizers, or filling agents, or sweeteners, or coloring agents. When they are present, these excipients are used as is conventional in an amount of 0.1 to 10% by weight of the total weight of the compression matrix, preferably 0.5 to 5% by weight.

According to one particular embodiment of the invention, the tablets are film-coated by means of an outer coating. For this purpose different grades of ethylcellulose or methacrylic polymers can be used, well known to persons skilled in the art.

The excipient(s) used for coating are applied in the manner known to persons skilled in the art, in the necessary quantity to obtain the desired function or functions.

These excipients can be applied to the surface of the tablet in conventional manner by spraying a solution or suspension of the coating agent in a solvent, in a perforated drum or fluidized bed for example.

When the polymer used for coating the tablet is a sustained-release polymer, the coated tablets according to the invention can advantageously be submitted to a maturation step of said coating polymer in order to secure its physical and chemical stability. This step is carried out under controlled temperature conditions, lower than the melting temperature of the active ingredient for a controlled period which depends on the coating polymer and which can take between 1 minute and several months, at 50 to 99% relative humidity. This step can be carried out in a drying oven or in a drum.

Coating can use an aqueous dispersion of ethylcellulose (Aquacoat® ECD-30, FMC) advantageously containing ethylcellulose in an amount of 2 to 5% by weight of the total weight of the coated tablets.

The opioids used within the scope of the invention are preferably naturally occurring or synthetic opium derivatives and/or alkaloids, such as codeine, narceine, noscapine, and salts thereof. Active materials suitable to be used according to the invention include compounds from the group comprising morphine, derivatives and salts thereof, and in particular morphinenes such as pholcodine, nalorphine, codeine, dihydrocodeine, hydromorphone, and morphinanes such as buprenorphine, butorphanol, dextromethorphane, nalbufine, naltrexone, naloxone, nalmefene, hydrocodone, oxymorphone and oxycodone, and in general all morphine analogs and all morphine analgesics, such as fentanyl, tramadol, apomorphine and etorphine.

The active ingredient(s) of the tablets according to the invention can amount to between 5 and 70% by weight of the total weight of the tablet. Advantageously the active ingredient(s) represent 10 to 50% by weight of the total weight of the tablet. The active ingredient(s) can be directly added to the compression mixture, coated onto carriers (to yield microgranule(s) or granulated by wet or dry processes (to yield granules).

When the active ingredient(s) are in the form of microgranules, these microgranules can be obtained as is conventional by depositing (layering) the active ingredient(s) onto the surface of pharmaceutically neutral carriers, such as prefabricated microspheres containing cellulose or a mixture of sugar and starch, and commercially available as "neutral core" or "sugar spheres", or other granulated excipients, e.g. such as lactose. The process for depositing (layering) the active ingredient is carried out in conventional manner and known to those skilled in the art, and can vary depending on the type, the amount and the fragility of the active ingredient(s) to be deposited. Thus, the depositing (layering) can be carried out by spraying a solution or suspension of the active ingredient(s) onto the surface the neutral carrier or by spraying the active ingredient(s) in the form of a powder onto the surface of the carrier previously wetted with a binder solution.

The granules of active ingredient(s) can also be obtained by dry or wet granulation of the active ingredient(s) of interest, generally in the presence of at least one binder and optionally a wetting liquid, likewise by techniques well known to those skilled in the art. The resulting granules are mixed with the excipients of the compression matrix then the mixture is compressed.

Advantageously, the granules comprising the active ingredient(s) of interest have a diameter suitable to give a good compression efficiency, i.e. generally between 100 and 600 μm.

According to another embodiment of the invention, and when its particle size so permits, the active ingredient is mixed directly with the excipients forming the compression matrix then the mixture is directly compressed.

Yet another alternative embodiment of the invention comprises mixing the active ingredient with the at least one excipient(s) of the compression matrix, then granulating this mixture using a dry or wet process in order to provide granules suitable for direct compression.

Advantageously, the total surface area of the tablet is less than 150 mm$^2$. The present invention is therefore suitable for making both low active strength tablets and high strength tablets.

The active ingredient can be mixed directly into the compression matrix or mixed in the form of granules or microgranules prepared beforehand. This granulation step improves the uniformity of the resulting tablet content. It is preferably performed by means of a wet process (with an aqueous or organic medium) for granules or by depositing (layering) the active ingredient from a solution or a suspension onto neutral carriers for microgranules.

The compression is carried out on a rotary tableting machine with a pre-compression station. The compression parameters should be selected so as to generate tablets whose hardness is suitable for the present invention.

Thus, according to the invention, one preferred embodiment of sustained-release matrix-type tablets comprises the following formulation:

| Ingredients | Percentage (%) |
|---|---|
| Granules | |
| Opioid | 10-50 |
| Binder | 0.1-10 |
| Polyvinyl acetate/polyvinyl pyrrolidone (80:20) | 35-45 |
| Microcrystalline cellulose | 35-45 |
| Coating | |
| Sustained-release polymer | 2-5 |
| Lubricants | 0.1-1 |
| Plasticizers | 0.1-2 |

Typically, the formulations of the present invention include an amount of opioid of between 1 to 400 mg, for example, 1, 2.5, 5, 10, 15, 25, 40, 50, 60, 80, 120, 160, 200, 300, and 400 mg.

The following examples are intended to illustrate the invention but cannot be construed as limiting the scope thereof.

EXAMPLES

Example 1

Production of Tablets Containing Granules Obtained by Granulation of Oxycodone HCl and HPMC and a Compression Matrix Consisting of a Mixture (1:1) of Two Excipients [Microcrystalline Cellulose and (PVA/Povidone 80:20)]
Preparation of the Tablets
1.1. Preparation of Oxycodone Granules The granules are obtained by wet granulation of the active ingredient (oxycodone HCl; Mc Farlan Smith, England) together with hydroxypropylmethylcellulose (HPMC grade Pharmacoat® 606, Brenntag) as a binder. The granulation is carried out in a fluidized bed (GCPG-I, Wurster, Glatt, Germany) by spraying, in bottom-spray mode, a solution of the binder (HPMC) onto the powdered active ingredient.

Oxycodone is added to the fluidized bed vessel and fluidized. The binding solution is sprayed onto the powder which agglomerates to form granules. The water is gradually evaporated off followed by a final drying step. The final drying step in a drying oven (16 hours at 60° C.) is performed in order to obtain a satisfactory, final water content (below 6%). The HPMC and oxycodone amounts are shown in Table 1.

TABLE 1

| Ingredients | Percentage [%] | Mass (g/batch) |
|---|---|---|
| Oxycodone HCl | 95.54 | 590.5 |
| HPMC (Pharmacoat ® 606) | 6.46 | 40.8 |
| Purified water | — | 483.9 |
| Total | 100.0 | 631.3 |

1.2. Preparation of the Compression Matrix

A pre-mixture of microcrystalline cellulose (Avicel ® PH102, FMC) and precipitated silica (Syloïd®244, Keyser & Mc Kay) is made in a cube mixer (AR401, Erweka) for 2 min at 40 rpm. The polyvinylacetate/povidone mixture (80:20) (Kollidon® SR, BASF) and the oxycodone granules prepared as described in step 1.1 are added to the pre-mixture and homogenized in a cube mixer for 15 minutes at 40 rpm. Finally the lubricant (magnesium stearate, Quimdis) for limiting adherence and compression friction is added to the mixture above with the following mixing parameters: 5 minutes at 40 rpm.

The amount of oxycodone granules used is determined in order to manufacture tablets containing 40 mg oxycodone.

The amounts of each of the excipients are reported in Table 2.

TABLE 2

| Ingredients | Percentage [%] | Mass (mg/tablet) |
|---|---|---|
| Tablets | 95.96 | 227.00 |
| HPMC (603) | 2.88 | 6.81 |
| Simethicone (dry weight) | 0.01 | 0.02 |
| Talc | 0.86 | 2.03 |
| Syloid ® 244 | 0.29 | 0.69 |
| Purified water** | N/A | N/A |
| Total (dry) | 100.00 | 234.5 |

1.3. Compression

The final mixture from the above step is submitted to a compression step on a tableting press (PR-12), Sviac) under a compression force of 35 kN with oblong punches having a size of 11 mm×5 mm. The compression is performed in conventional manner with neither the compression mixture nor the compression tools being submitted to a heating step prior to or during the actual compression step.

1.4 Coating 1.4.1 Sub-Coating

Prior to coating with the actual polymer, a sub-coating step is performed on the tablets.

This sub-coat is intended to improve to surface condition of the tablets. It consists of a mixture of HPMC (Pharmacoat®603) an anti-foaming agent (Simethicone, Dow Corning), a lubricant (micronized talc, Luzenac (Univar) and an anti-static agent (Syloid®244, Keyser & McKay) so that the HPMC represents a weight gain of 3% relative to the total weight of the uncoated tablets. The proportions of each of the excipients are given in Table 3.

This sub-coating is conducted as is conventional in a perforated drum (Trislot).

1.4.2. Coating

The actual coating of the previously sub-coated tablets is also performed in a perforated drum (Trislot).

Coating is conducted from an aqueous dispersion of ethylcellulose (Aquacoat® ECD-30, FMC) with a proportion of ethylcellulose representing 2.87% by weight of the total weight of the coated tablets. The proportion of the different excipients is given in Table 3. Here again, no specific heating step of the tablets is carried out either before or during the application of the sub-coating or actual coating.

TABLE 3

| Ingredients | Percentage [%] |
|---|---|
| Tablets | 95.75 |
| Aquacoat ® ECD-30 dry) | 2.87 |
| Dibutyl sebacate | 0.69 |
| Talc | 0.52 |
| Syloid ® 244 | 0.17 |
| Purified water** | N/A |
| Total (dry) | 100.0 |

**The water is removed during the process;
N/A: Not Applicable

Pharmacokinetic Study
1. Pharmacokinetic Study in Healthy Volunteers

The produced 40 mg tablets were also tested in vivo in order to determine the plasma oxycodone profile in healthy volunteers administered with a dose of said tablets.

A pharmacokinetic study was carried out in 12 healthy, fasting male and female volunteers who were divided into two half-groups.

Each half-group was given both treatments sequentially (tablets of the invention and reference drug) after an intermediate wash-out period.

The reference drug used in this study is Oxycontin®, a sustained-release oxycodone tablet administered twice a day, also of 40 mg strength.

The plasma concentrations (expressed in ng/ml) for the measurement of the changes of blood concentrations of oxycodone in blood were determined by taking blood samples at the followings times: prior to administration (t=0), then at 0.5, 1, 1.5, 2, 2.5, 3, 3.5, 4, 5, 6, 8, 10, 12, 14, 16, 20, 24, 30, 36 and 48 h after administration of the product (tablet of the invention or reference drug depending on randomization).

The plasma concentrations of oxycodone were measured in 12 healthy subjects after one single oral dose. The resulting pharmacokinetic parameters are given in Table 4.

TABLE 4

| Parameters | Test (invention) (n = 12) | | Reference Oxycontin® (n = 12) | |
|---|---|---|---|---|
| | Mean | CV % | Mean | CV % |
| $C_{max}$ (ng/mL) | 34.412 | 20 | 53.129 | 25.0 |
| $T_{max}$ (hours) | 10.0 | 16.6 | 3.00 | 34.3 |
| $AUC_t$ (ng h/mL) | 667.109 | 16.9 | 611.848 | 21.9 |
| $AUC_\infty$ (ng h/mL) | 679.846 | 17.1 | 614.960 | 21.7 |
| $AUC_{t/\infty}$ (%) | 98.17 | 1.7 | 99.48 | 0.3 |
| $K_{el}$ (hours$^{-1}$) | 0.1154 | 24.0 | 0.1561 | 16.4 |
| $T_{1/2}$ el (hours) | 6.39 | 28.0 | 4.56 | 17.2 |

Note:
For the $T_{max}$ values, the median value is indicated;
CV: Coefficient of variation in %;
$K_{el}$: elimination rate constant;
$T_{1/2}$ el: elimination half-life 2. In Silico Study: Steady-State Pharmacokinetic Simulation by "Interpolation-Addition" from the Single Dose Results.

The calculated bioavailability of the tablet of the invention is compared with that of a reference oxycodone formulation (OxyContin® at 40 mg), after calculation of the steady-state profiles of each of the volunteers from their own single dose profile (simulation of a repeat dose over 4 days in 12 healthy volunteers). The mean profile and the mean parameters are therefore the mean of individual profiles and individual parameters. Thus, the inter-individual variability is accounted for in the calculation.

The calculated steady-state pharmacokinetic parameters of the oxycodone are shown in the following Table 5:

TABLE 5

| | Steady-state 40 mg OxyContin® (calculated) | | Steady-state test Oxycodone (invention) at 40 mg (calculated) | |
|---|---|---|---|---|
| | Mean parameter | Min-Max | Mean parameter | Min-Max |
| Cssmax (ng/ml) | 74.25 | 62-121 | 62.7 | 48-79.5 |
| Cssmin (ng/ml) | 29.3 | 21.9-41.7 | 50.7 | 36.7-65.5 |
| Swing (%) | 156.6 | 105.7-218.7 | 24.1 | 12.8-43.7 |
| Fluctuation (%) | 87.9 | 66.6-117.2 | 21.4 | 12.1-37 |
| Cav (ng/ml) | 51.2 | 39.4-79.2 | 56.5 | 43.4-69.6 |
| AUCsst (ng/ml · h) | 614.6 | 472.4-950.4 | 678.4 | 520.9-835.7 |
| Cssmax-Cssmin (ng/ml) | 60.5 | 54.3-65.5 | 19.1 | 14.4-30.4 |

The "fluctuation" and "swing" parameters of the formulation according to the invention show rounded values of 21 and 24% respectively.

3. In Silico Bioequivalence: Bioequivalence from the Calculated Individual Parameters

| | Ratio | 90% Confidence interval |
|---|---|---|
| AUCt | 113.3 | 105.3-121.9 |
| Swing | 14.34 | 11.84-17.35 |
| Fluctuation | 22.53 | 19.08-26.6 |

The "fluctuation" and "swing" parameters, with respect to the reference, show a ratio of 14.3% and 22.5%, respectively, i.e. a decrease of 85% and 77%.

Example 2

1. Production of Film-Coated Tablets Using an Outer Coating of Aquacoat® ECD-30 (Ethylcellulose) Containing Granules Obtained by Granulating HCl Oxycodone and HPMC, and a Compression Matrix Consisting of a (1:1) Mixture of Two Excipients [Microcrystalline Cellulose and (PVA/Povidone 80:20)].

Preparation of the Tablets 1.1. Preparation of Oxycodone Granules

The granules are obtained by wet granulation of the active ingredient (oxycodone HCl; Mc Farlan Smith, England) together with hydroxypropylmethylcellulose (HPMC grade Pharmacoat® 606, Brenntag) as a binder. The granulation is carried out in a fluidized bed (GCPG-I, Wurster, Glatt, Germany) by spraying, in bottom-spray mode, a solution of the binder (HPMC) onto the powdered active ingredient.

Oxycodone is added to the fluidized bed and fluidized. The binding solution is sprayed onto the powder which agglomerates to form granules. The water is gradually evaporated off followed by a final drying step. The final drying step in a drying oven (16 hours at 60° C.) is performed in order to obtain a satisfactory final water content (below 6%). The HPMC and oxycodone amounts are shown in Table 6.

TABLE 6

| Ingredients | Percentage [%] |
|---|---|
| Oxycodone HCl | 95.9 |
| HPMC (Pharmacoat ® 606) | 4.1 |
| Purified water | — |
| Total | 100.0 |

1.2. Preparation of the Compression Matrix

A pre-mixture of microcrystalline cellulose (Avicel (® PH102, FMC) and precipitated silica (Syloïd®244, Keyser & Mc Kay) is made in a cube mixer (AR401, Erweka) for 2 min at 40 rpm. The polyvinylacetate/povidone mixture (80:20) (Kollidon® SR, BASF) and the oxycodone granules prepared as described in Step 1.1 are added to the pre-mixture and homogenized in a cube mixer for 15 minutes at 40 rpm. Finally the lubricant (magnesium stearate, Quimdis) for limiting adherence and compression friction is added to the above mixture with the following mixing parameters: 5 minutes at 40 rpm.

The amount of oxycodone granules used is determined to produce tablets containing 40 mg oxycodone.

The amounts of each of the excipients are summarized in Table 7.

TABLE 7

| Ingredients | Percentage [%] | Mass (mg/tablet) |
|---|---|---|
| Oxycodone granules | 19.47 | 43.80 |
| Kollidon ® SR | 39.92 | 89.81 |
| Avicel ® PH102 | 39.92 | 89.81 |
| Syloïd ® 244 | 0.20 | 0.46 |
| Magnesium stearate | 0.50 | 1.13 |
| Total | 100.00 | 225.00 |

1.3. Compression

The final mixture from the preceding step is submitted to a compression step on a tableting press (PR-12), Sviac) under a compression force of 35 kN with oblong punches having a size of 11 mm×5 mm. The compression is performed in a conventional manner with neither the compression mixture nor the compression tools being submitted to a heating step prior to or during the actual compression step.

1.4. Coating

The actual coating of the tablets is also performed in a perforated drum (Trislot or Glatt).

The tablets are coated from an aqueous dispersion of ethylcellulose (Aquacoat® ECD-30, FMC) with an amount of ethylcellulose representing 2.87% by weight of the total weight of the coated tablets. The amount of the various excipients is shown in Table 8.

Here again, the tablets are not submitted to any specific heating step either prior to or during actual coating.

TABLE 8

| Ingredients | Percentage [%] |
|---|---|
| Tablets | 95.75 |
| Aquacoat ® ECD-30 (dry) | 2.87 |
| Dibutyl sebacate | 0.69 |
| Talc | 0.52 |

TABLE 8-continued

| Ingredients | Percentage [%] |
|---|---|
| Syloïd ® 244 | 0.17 |
| Purified water ** | N/A |
| Total (dry) | 100.00 |

** Note:
the water is removed during the process;
N/A: Non Applicable

2. Pharmacokinetic Study with Repeat Doses in Healthy Volunteers: Characterization of the Pharmacokinetic Profile of the Tablet of the Invention in Steady-State A pharmacokinetic study was conducted in 30 healthy male and female fasting volunteers separated into two half-groups.

Each half-group was given both treatments sequentially (tablets of the invention and reference drug), each administered twice-a-day for 5.5 days (11 treatments per period) after an intermediate wash-out period.

The reference drug used in this study is Oxycontin®, a sustained-release oxycodone tablet administered twice a day, also of 40 mg strength.

The plasma concentrations (expressed in ng/ml) for the measurement of changes in blood concentrations of oxycodone were determined by taking blood samples at the followings times:

- prior to administration on days 4 and 5 to verify that a steady-state had been reached,
- then 5 minutes before the last administration (day 6) and 1, 1.5, 2, 2.5, 3, 3.5, 4, 5, 6, 7, 8, 10, 12, 14, 16, 20, 24, 36 and 48 h after the last administration of the product (tablet of the invention or reference drug depending on randomization).

The plasma concentrations of oxycodone were measured in 30 healthy subjects after repeat administrations every 12 hours of an oral dose of 40 mg.

The pharmacokinetic parameters of oxycodone observed in the steady-state are reported in following Table 9.

TABLE 9

| | Steady-state 40 mg Oxygesic ® (calculated) | | Steady-state test Oxycodone (invention) | |
|---|---|---|---|---|
| | Average parameter | CV (%) | Average parameter | CV (%) |
| Cssmax (ng/ml) | 63.792 | 20.7 | 51.719 | 25.3 |
| Cssmin (ng/ml) | 26.299 | 27.2 | 36.890 | 40.2 |
| Swing (%) | 148.13 | 22.9 | 70.38 | 113 |
| Fluctuation (%) | 83.86 | 16.8 | 42.86 | 57.6 |
| Cav (ng/ml) | 45.411 | 23.0 | 42.365 | 27.0 |
| AUCsst (ng/ml · h) | 544.937 | 23.0 | 508.381 | 27.0 |
| Cssmax-Cssmin (ng/ml) | 17.65 | 8.66 | 37.49 | 8.37 |

The "fluctuation" and "swing" parameters of the formulation according to the invention show rounded values of 43 and 70% respectively.

The "fluctuation" and "swing" parameters, with regard to the reference, show a ratio of 44% and 33%, respectively, i.e. a decrease of 56% and 67%.

CONCLUSION

From a pharmacokinetic viewpoint, the characteristics of the present invention have demonstrated the following advantages:
- Reducing steady-state peak concentration values, while maintaining the same AUC values (same bioavailability)
- Decreasing steady-state fluctuations (fluctuation and swing parameters, difference between Cssmax and Cssmin)
- Maintaining concentrations at a level greater than 75% of Cssmax for an extended period of time.

From a clinical viewpoint, the release characteristics of the dosage forms of a pharmaceutically active substance have revealed the following advantages:
- Maintaining efficient and virtually constant steady-state plasma concentrations (essentially without either fluctuation or swing) upon chronic treatment, with repeat dosing of the dosage form of the present invention at intervals of 12 hours.
- Maintaining steady-state plasma concentrations at a lower level, thus limiting the occurrence of side effects such as nausea, drowsiness or other cognitive side effects.
- Limiting "peaks and troughs" while limiting the occurrence of resurgent pain related to plasma concentrations, and limiting breakthrough pain.

The invention claimed is:

1. A method of treatment of severe pain comprising administering orally to a patient in need thereof in a repeated manner twice-a-day a sustained-release matrix-type tablet releasing at least one opioid or one of its pharmaceutically acceptable salts, said matrix-type tablet comprising:
   a compression matrix consisting of granules of one opioid or one of its pharmaceutically acceptable salts and hydroxypropylmethylcellulose (HPMC); a mixture of microcrystalline cellulose and polyvinyl acetate/polyvinyl pyrrolidone (80:20); precipitated silica; and magnesium stearate;
   a sub-coating consisting of a mixture of hydroxypropylmethylcellulose (HPMC), simethicone, micronized talc, and precipitated silica; and
   a coating consisting of a mixture of an aqueous dispersion of ethylcellulose, dibutyl sebacate, talc, and precipitated silica;
   wherein each administration being spaced apart by 8 to 14 hours, said method maintaining the steady-state opioid plasma concentration obtained in vivo with a reduced fluctuation at above 60% of the $Css_{max}$ value for at least 10 hours.

2. The method of claim 1, characterized by a "swing" parameter of less than 50%.

3. The method of claim 1, characterized by a "fluctuation" parameter of less than 50%.

4. The method according to claim 1, characterized by a reduction in plasma fluctuations and in peaks and troughs, by limitation of resurgent pain due to lowered concentrations, and by limitation of episodes of acute pain.

5. The method of claim 1, characterized by a reduction in some side effects such as nausea, drowsiness and other cognitive side effects.

6. The method of claim 1, wherein the opioid is selected from the group consisting of codeine, narceine, noscapine, morphine, pholcodine, nalorphine, dihydrocodeine, hydromorphone, buprenorphine, butorphanol, dextromethorphane, nalbufine, naltrexone, naloxone, nalmefene, hydrocodone, oxymorphone and oxycodone, fentanyl, tramadol, apomorphine and etorphine, or a pharmaceutically acceptable salt thereof.

7. The method of claim 1, wherein the opioid is oxycodone hydrochloride.

8. The method of claim 1, wherein each administration is spaced apart by 10 to 13 hours.

9. The method of claim 1, wherein the steady-state opioid plasma concentration obtained in vivo is maintained with a reduced fluctuation at above 75% of the $Css_{max}$ value.

10. The method of claim 1, wherein said steady-state opioid plasma concentration obtained in vivo is maintained with a reduced fluctuation for at least 12 hours.

* * * * *